United States Patent [19]

Chaumette et al.

[11] Patent Number: 5,112,591
[45] Date of Patent: May 12, 1992

[54] PROCESS FOR PREPARING PRECURSORS OF CATALYSTS CONTAINING COPPER, ALUMINUM AND ZINC, USABLE FOR THE SYNTHESIS AND THE DECOMPOSITION OF METHANOL

[75] Inventors: Patrick Chaumette, Bougival; Fabienne Le Peltier, Rueil-Malmaison; Raymond F. Szymanski, Maisons Lffitte; Philippe Courty, Houilles; Catherine Verdon, Rueil-Malmaison, all of France

[73] Assignee: Institut Francais du Petrole, Rueil-Malmaison, France

[21] Appl. No.: 656,892

[22] Filed: Feb. 19, 1991

Related U.S. Application Data

[62] Division of Ser. No. 514,059, Apr. 24, 1990, Pat. No. 5,019,547.

[30] Foreign Application Priority Data

Apr. 24, 1989 [FR] France .............................. 89 05424

[51] Int. Cl.⁵ ...................... C01B 3/22; C01B 31/18; C07C 27/06
[52] U.S. Cl. ............................. 423/415 A; 252/373; 423/648.1; 423/437; 518/713
[58] Field of Search ................... 518/713; 423/415 A, 423/648.1, 437; 252/373

[56] References Cited

U.S. PATENT DOCUMENTS

| | | | |
|---|---|---|---|
| 3,971,735 | 7/1976 | Asano et al. | 518/713 |
| 4,091,086 | 5/1978 | Hindin et al. | 423/648.1 |
| 4,436,833 | 3/1984 | Broecker et al. | 502/176 |
| 4,631,266 | 12/1986 | Wold et al. | 423/648.1 |
| 4,788,175 | 11/1988 | Short et al. | 518/713 |
| 4,801,574 | 1/1989 | Brown et al. | 518/713 |
| 4,956,392 | 9/1990 | Saito et al. | 518/713 |

Primary Examiner—Wayne Langel
Attorney, Agent, or Firm—Millen, White & Zelano

[57] ABSTRACT

The present invention relates to a process for preparing a precursor of a catalyst containing copper, aluminum and zinc.

This precursor is formed by the mixing of two ternary precursors, at different stages of their manufacturing, these two ternary precursors being different from one another in their metallic stoichiometry (atomic ratios between Cu, Zn and Al), in their crystallographic structure and in their elemental morphology.

The catalyst obtained from this precursor can be used in particular for the synthesis of methanol.

23 Claims, 3 Drawing Sheets

PROCESS FOR PREPARING PRECURSORS OF CATALYSTS CONTAINING COPPER, ALUMINUM AND ZINC, USABLE FOR THE SYNTHESIS AND THE DECOMPOSITION OF METHANOL

This is a division of application Ser. No. 07/514,059, filed Apr. 24, 1990, now U.S. Pat. No. 5,019,547, issed May 28, 1991.

SUMMARY OF THE INVENTION

The present invention relates to a process for preparing a precursor, preferably hydroxycarbonated, of a catalyst that can be used in particular in processes utilizing a balanced reaction of the carbon oxides (CO, $CO_2$) with hydrogen, particularly the production of methanol from synthesis gas and the decomposition reactions of the primary alcohols and particularly pf methanol or ethanol in a mixture containing carbon oxides and hydrogen.

This precursor is formed, according to the invention, by the association or the mixing, for example on the micrometric scale or a scale inferior to the micrometer, of two ternary precursors (either in the hydrated form, or in the oxide form if they have been subjected to a final calcination) comprising each the following three metals: copper, aluminum and zinc. The association (or the mixing) of these two ternary precursors is in particular characterized by the fact that said ternary precursors are different from one another at the same time in their metallic stoichiometry (atomic ratios between Cu, Zn and Al), their crystallographic structure and their elemental morphology. This mixing of said ternary precursors can be achieved at different stages of their manufacturing.

BACKGROUND OF THE INVENTION

Copper and zinc oxide-based catalysts have been known for many years; they have been described as soon as 1933 by DODGE (US-A-1,908,696). In U.S. Pat. Nos. 3,388,972, 3,546,140 and 3,790,505, the US company C.C.I. describes the use of Cu, Zn, Al ternary compositions for the conversion at low temperature of carbon oxide (CO) and for the synthesis of methanol.

Various methods for preparing Cu, Zn, Al catalysts are especially described in U.S. Pat. Nos. 3,923,694, 4,279,781, 4,596,782 and FR-A-2,352,588.

FR-A-2,352,588 describes the preparation of a catalyst through the mechanical mixing of 10 to 60% of copper oxide, 5 to 40% of zinc oxide and 30 to 70% of an aluminous cement, as well as the use of this catalyst for the conversion of the carbon oxide in order to produce hydrogen or methanol.

Apart from the catalyst described in FR-A-2,352,588, these catalysts are generally produced by a precipitation reaction between an acid solution containing for example the nitrates of the metals cited above and a basic solution containing for example an alkaline carbonate. The precipitation reaction, such as that which is for example described in U.S. Pat. No. 3,923,694, leads to obtaining hydrated precursors, at least partly crystallized, consisting of at least three phases: a CuAlZn ternary phase, with (Cu+Zn)/Al=3 (atoms.atom-1), of the hydrotalcite type; a binary phase, the rosacite, which is a mixed copper and zinc hydroxycarbonate; and a copper hydroxycarbonate, the malachite, and possibly also other phases, such as for example the $ZnAl_2O_4$ spinel described in U.S. Pat. No. 3,923,694.

The consequence of the heterogeneousness of composition of these catalysts is relatively low activity, selectivity and stability, even though they initially contain a copper oxide that is well-dispersed, at least partly. Various publications, as for example F. TRIFIRO et al, Preparation of Catalysts III, p. 723–733, 1983, Elsevier Science Publishers (Amsterdam), give a detailed description of the simultaneous forming of these phases.

The preparation of copper-based catalysts obtained by the calcination of identified crystallized precursors, and more particularly of hydroxycarbonated phases obtained by co-precipitation, has been rarely described. U.S. Pat. No. 4,145,400 describes the preparation of CuZnAl catalysts, but said catalysts are prepared from only one crystallized monophase precursor, hydrotalcite. As for U.S. Pat. No. 4,596,782, it describes the preparation of a methanol synthesis catalyst from only one amorphous hydrated precursor with a very high homogeneity. On the other hand, the catalyst described in U.S. Pat. No. 4,436,833 is prepared from the mixture of a binary crystallized phase of formulation $Cu_{2.2}Zn_{2.8}(OH)_{16}(CO_3)_2$ and of aluminum hydroxyde. Lastly, U.S. Pat. No. 3,923,694 describes a sequential coprecipitation where a spinel precursor containing aluminum and zinc is first obtained, then a binary Cu-Zn compound is co-precipitated on this precursor. In numerous documents, for example U.S. Pat. No. 3,388,972, 3,546,140, FR-A-2,027,162, the alumina, which is the main component of the catalyst, is introduced in the oxide state or else in the hydroxyde state (U.S. Pat. No. 4,279,781).

Figure 1:
FIG. 1 shows the prespinel phase of the present invention.

The precursor, preferably hydroxycarbonated, can be obtained according to the invention by mixing together two ternary precursors, preferably hydroxycarbonated, each comprising at least copper, aluminum and zinc, one of said ternary precursors containing at least 50%, preferably at least 65%, and, more preferably, at least 85% by weight of a phase called "roderite" defined hereafter, and the other one of said ternary precursors containing at least 50% preferably at least 65%, and more preferably, at least 85% by weight of a phase called "prespinel" defined hereafter.

It seems that the roderite phase has already been examined, but badly characterized by DOESBURG E.B.M. (Univ. DELFT), HOPPENER (DSM, Studies in Surface Science and Catalysis Vol. 31, p. 767, 1987); still the same authors declare that the most active catalysts do not contain this phase, but a mixture of the rosacite and hydrotalcite phases. Moreover, one of these phases (rosacite) merely consists of the two elements copper and zinc, contrarily to the two ternary precursors used in the present invention, which contain the three elements Cu,Zn,Al. The prespinel phase has not been described to date.

As shown through the microanalyses by X-ray emission spectrometry carried out by the applicant, the elemental roderite and prespinel phases show a different ternary composition in Cu, Zn and Al:

the roderite phase shows an atomic ratio (Cu+Zn)/Al ranging from 3.5 to 16 and preferably from 4 to 13, and an atomic ratio Zn/Al ranging from 1.6 to 6 and preferably from 2 to 5;

the prespinel phase shows an atomic ratio (Cu+Zn)/Al ranging from 0.20 to 2.10 and preferably from 0.25 to 1.50, and an atomic ratio Zn/Al ranging from 0.10 to 1.50 and preferably from 0.15 to 1.20.

Said elemental phases, the precursors and the catalysts of the present invention can be characterized by an X-ray emission spectrometry in a scanning transmission electron microscope. The analyses are carried out for example by means of a device which can give high-resolution images (0.5 to 1 nm) in the STEM mode and shows a high sensitivity in the X-ray micro-analysis mode. A commercial device such as the scanning transmission electron microscope Vacuum Generator HB 501, equipped with a Si-Li KEVEX detector associated with a TRACOR analyzer, is quite suitable (sensitivity limit higher than 1,000 atoms of a given element) for determining the morphology and the local composition of the precursors and catalysts. In order to preserve the organization of the phases between each other and to describe their macroscopic distribution in the coprecipitate grains during the preparation of the precursors (see hereafter) better, a preparation method using an ultramicrotom cutting in order to obtain grain sections with a thickness of several tens of nanometers (1 nm=$10^{-9}$ m) can be used.

Thus, after selecting the zone to be analyzed (typically 2 to 5 nm), several countings of a duration of 100-1000 s, leading to a sufficiently precise counting statistic (over 10%), are simultaneously performed.

From the intensities that are measured on the various peaks selected for the different elements that are present in the sample, it is possible to determine their relative concentrations, then their respective atomic ratios, according to well-known X-ray emission techniques (see for example REED S. J. B. Electron microprobe Analysis, Cambridge University Press, 1975), for each of the particles constituting the sample.

The samples that are compared must all show the same thickness. The average values of the coefficients of correction (reduced to Cu-K $\alpha=1$) are the following

| Line measurements | Element | Coefficient |
|---|---|---|
| K $\alpha$ | copper | 1 |
| K $\alpha$ | aluminum | 4.86 |
| K $\beta$ | zinc | 4.68 |

These coefficients have been determined by the applicant from mixed oxides calcined at a high temperature: $CuAl_2O_4$, $ZnAl_2O_4$, $Cu_{1-x}Zn_xAl_2O_4$ (x=0.25-0.50-0.75) are the reference samples.

The atomic ratio Zn/Al is for example calculated as follows (iK$\beta$ Zn and iK$\alpha$Al are the average rough intensities determined through several countings):

Zn/Al=0.963 $i_{K\beta}Zn/i_{K\alpha}Al$.

The best results, in terms of activity, selectivity and stability, are generally obtained with catalysts for which each monophase (roderite, prespinel) shows a variation of the atomic ratios (Cu+Zn)/Al and Zn/Al lower than about 15% and preferably lower than about 10% in relation to the average value of this ratio, at the scale of 5 nanometers.

Figure 2:
FIG. 2 shows the roderite phase of the present invention.

The prespinel phase has a grained aspect with little contrasts (FIG. 1, where 1 cm represents 100 nm), whereas the roderite phase shows a fibrillary morphology, the length of the fibers ranging from about 50 to about $900.10^{-10}$ m and their diameter ranging from about 5 to about $100.10^{-10}$ m (FIG. 2, where 1 cm represents 48 nm). It is thus possible to distinguish these two phases by electronic microscopy and to determine their atomic ratios (Cu+Zn)/Al and Zn/Al. Each one of the phases shows a homogenous composition at least at the scale of one nanometer, controlled by X-ray emission spectrometry.

X-ray diffraction can also be utilized for characterizing the roderite and prespinel phases, the precursors and the catalysts. The X-ray diffraction diagrams of each sample are for example recorded on a Philips PW 1050 goniometer using the $K_\alpha$ line of cobalt. The study of the X-ray diffraction diagrams shows certain features of the 2 prespinel and roderite phases, preferably hydroxycarbonated:

the micro-crystallized prespinel phase is identified in the dried state by an extensive amorphous background and wide bands located at 4.7; 2.87; 2.49 and $1.43.10^{-10}$m;

the roderite phase is easily identified in the dried state from the lines located at 6.8; 4.5 and $3.3.10^{-10}$m; these last two lines especially allow to distinguish it from the zinc hydroxycarbonated structures $Zn_5(OH)_6(CO_3)_2$ and $Zn_4(OH)_2(CO_3)_3 4H_2O$.

Figure 3:
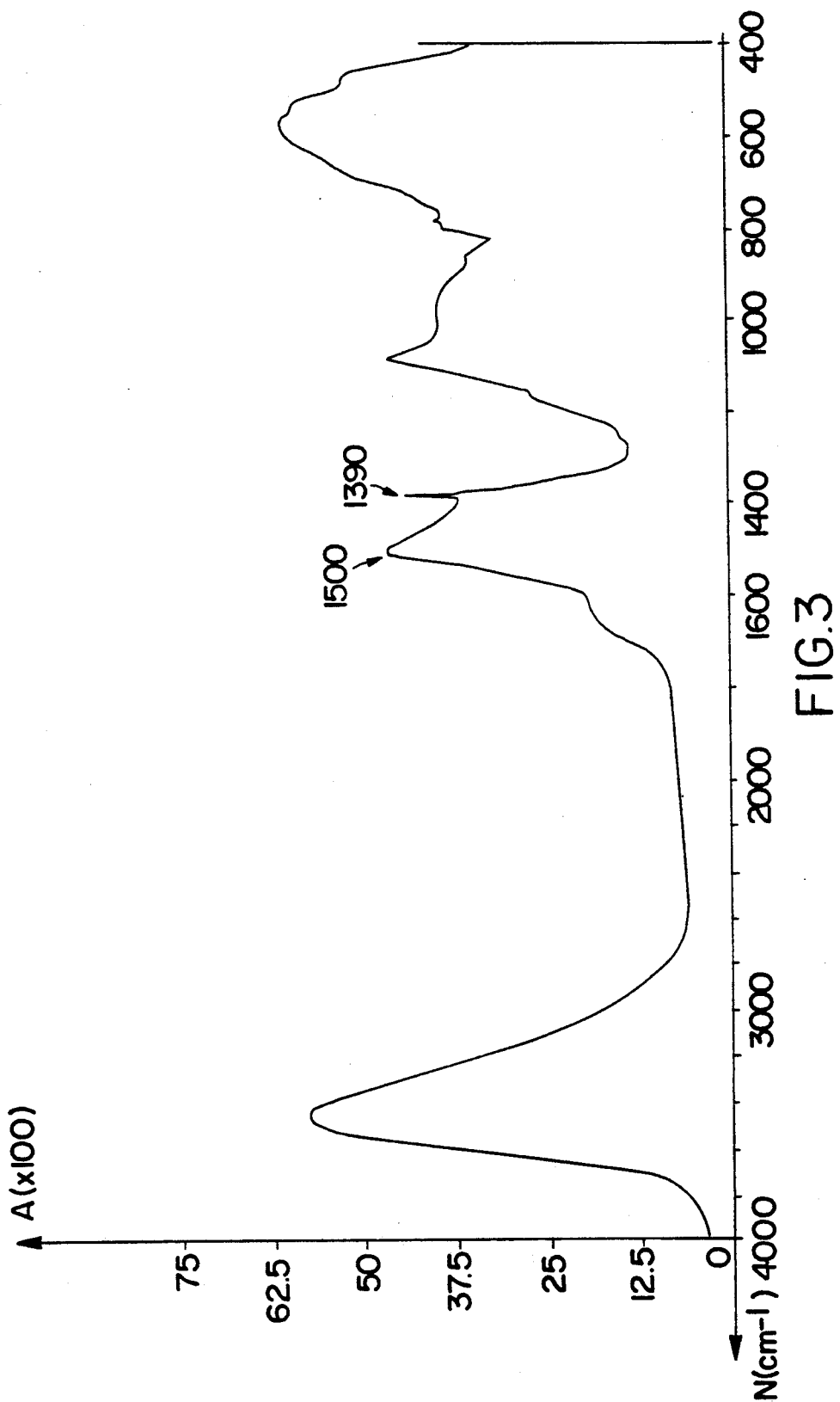
FIG. 3 shows the band width of the prespinel phase of the present invention.
Figure 4:
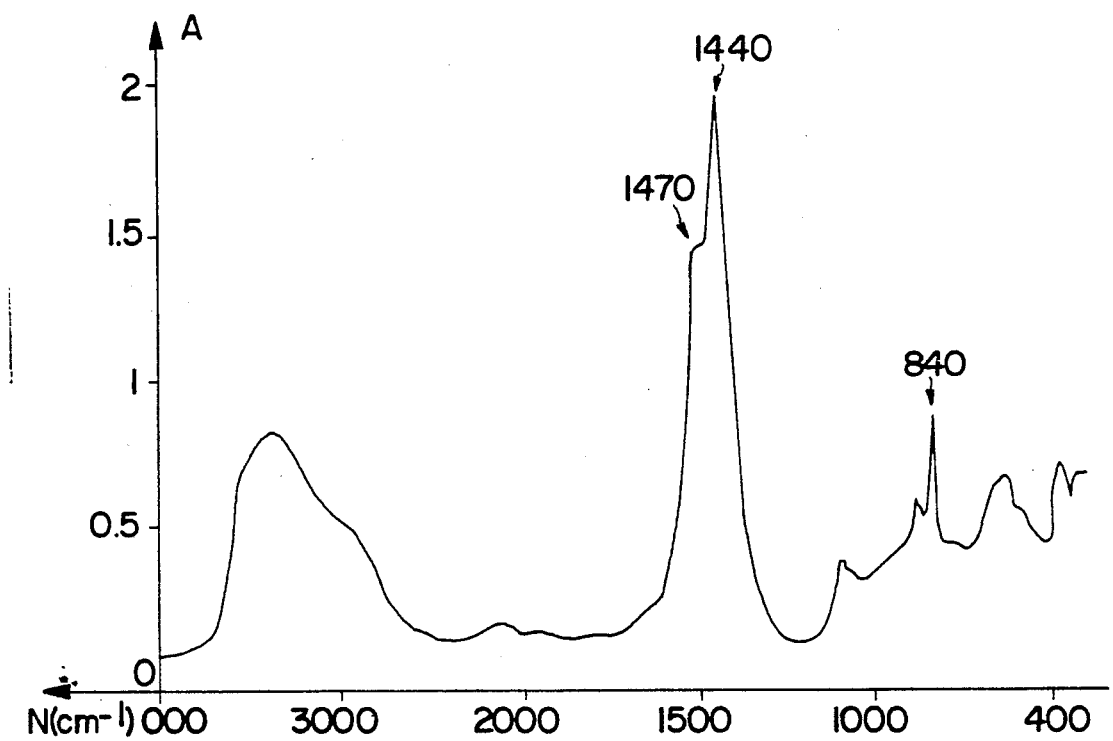
FIG. 4 shows the band width of the roderite phase of the present invention.

Another technique allowing to confirm the presence of the two prespinel and roderite phases, preferably hydroxycarbonated, in a co-precipitated or dried sample, consists in recording an infrared spectrum of said sample (before calcination). The infrared spectrums are achieved by means of a spectrometer, for example of the DIGILAB FTS 15E type, allowing a Fourrier Transformed-Infra Red (F.T.-I.R.) spectroscopy, the sample (1 mg) being admixed with KBr (300 mg), then pelletized:

the prespinel phase is characterized by a $\gamma(CO_3^{2-})$ vibration, leading to a wide band the maximum of which is located at 1,500 cm$^{-1}$ and to a narrow band at 1,390 cm$^{-1}$ (table 1 and FIG. 3);

on the contrary, the roderite phase shows $\gamma(CO_3^{2-})$ vibrations in the form of a doublet at 1,440 and 1,470 cm$^{-1}$ and a faint peak at 840 cm$^{-1}$ (table I and FIG. 4).

Figure 5:
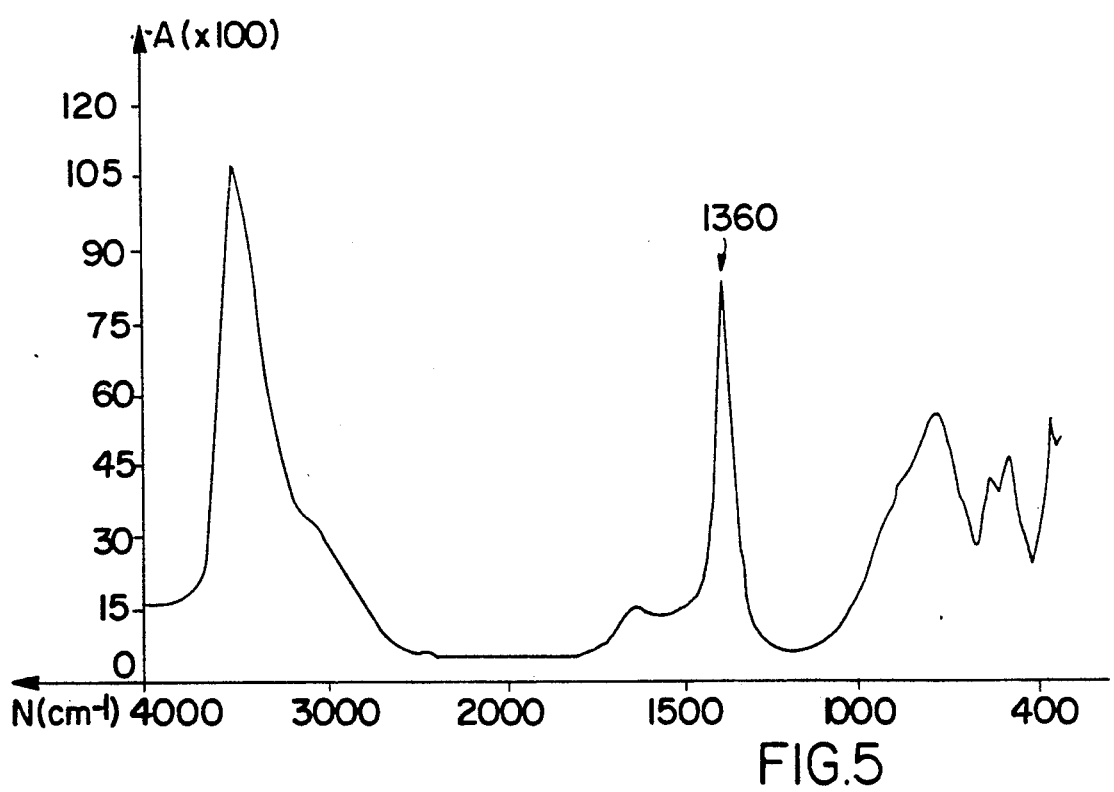
FIG. 5 shows the band of the hydrotalcite phase described in U.S. Pat. No. 4,145,400.

These bands thus allow to detect the presence of these two phases and to distinguish them from the hydrotalcite phase especially described in U.S. Pat. No. 4,145,400, the characteristic vibration of the carbonate groups of which, $\gamma(CO_3^{2-})$, is located at 1,360 cm$^{-1}$ (table I and FIG. 5). In FIGS. 3 to 5, A represents the absorbance and N, the number of waves (in cm$^{-1}$).

| PHASE | $\nu(CO_3^{2-})$ | (cm$^{-1}$) |
|---|---|---|
| PRESPINEL | | 1,390 1,500 |
| RODERITE | 840 | 1,440 1,470 |
| HYDROTALCITE | — | 1,360 — |

The roderite phase and the prespinel phase represent together at least 50%, preferably at least 65%, and, more preferably, at least 85% by weight of the precursor, preferably hydroxycarbonated, prepared according to the invention. When the intimate association roderite-prespinel does not constitute 100% by weight of said precursor, the 100% complement can consist of:

one or several amorphous or mrcrocrystallized phases, not detectable by X-ray diffraction, comprising at least one of the metals selected from the group consisting of copper, aluminum and zinc, and/or one or several crystallized phases such as hydrotalcite, rosacite, malachite, hydrozincite (the presence of basic copper hydroxynitrate (or gerarhdite) will preferably be avoided).

DETAILED DESCRIPTION OF THE INVENTION

Thus, the object of the present invention is a process for preparing a precursor, preferably hydroxycarbonated, of a catalyst containing copper, aluminum and zinc, at least 50%, preferably at least 65% and, more preferably, at least 85% by weight of said precursor being made up of the mixing of a phase called roderite consisring of copper, aluminum and zinc and showing an atomic ratio $(Cu+Zn)/Al$ ranging from 3.5 to 16, preferably from 4 to 13 and an atomic ratio $Zn/Al$ ranging from 1.6 to 6, preferably from 2 to 5, and of a phase called prespinel, which is another object of the invention, consisting of copper, aluminum and zinc and showing an atomic ratio $(Cu+Zn)/Al$ ranging from 0.20 to 2.10, preferably from 0.25 to 1.50 and an atomic ratio $Zn/Al$ ranging from 0.10 to 1.50, preferably from 0.5 to 1.20. Said process is characterized in that said precursor results from the mixing (or compounding) of two ternary precursors, preferably hydroxycarbonated, each of them comprising copper, aluminum and zinc, one of said ternary precursors containing at least 50%, preferably at least 65%, and more preferably at least 85% by weight of roderite phase and the other one of said ternary precursors containing at least 50%, preferably at least 65% and more preferably at least 85% by weigt of prespinel phase, said mixing (or said compounding) taking place between, on one hand, one of the ternary precursors obtained at the end of one of stages 1/ to 4/ of a process P comprising the following stages:

1/ co-precipitation reaction within a reactor previously containing water (for example bi-permuted), between an aqueous solution of at least one compound of a constituent selected from the group consisting of the alkali metals (such as sodium, potassium) and the ammonium ion, said compound being selected from the group consisting of the carbonates, the hydrogenocarbonates and the hydroxydes, and an aqueous solution containing, in the form of compounds selected from the group consisting of the soluble salts and the soluble complexes (preferably soluble in an acid medium), copper, aluminum and zinc in such proportions that the atomic ratio $(Cu+Zn)/Al$ ranges from 3.5 to 16, preferably from 4 to 13, and the atomic ratio $Zn/Al$ ranges from 1.6 to 6, preferably from 2 to 5, said reaction taking place at a pH value usually ranging from 6.3 to 7.3, preferably from 6.7 to 7.1, at a temperature generally ranging from 70° to 90° C., preferably from 75° to 85° C., with an average time of residence in..=the reactor ranging from 0.1 to 60 minutes, preferably from 10 to 45 minutes (this average residence time is defined as the inverse value of the ratio of the total volume flow rate (in liters/minute) of the solutions injected into the reactor to the volume of said reactor (in liters)), 2/ filtration, then water washing of the product obtained at the end of stage 1/, 3/ drying of the product obtained at the end of stage 2/, between 50° and 200° C., 4/ calcination of the product obtained at the end of stage between 250° and 500° C., preferably between 280° and 380° C.;

and, on the other hand, one of the ternary precursors obtained at the end of one of stages 1/ to 4/ of a process P' comprising the following stages:

1/ co-precipitation reaction within a reactor previously containing water (for example bi-permuted), between an aqueous solution of at least one compound of a constituent selected from the group consisting of the alkali metals (such as sodium, potassium) and the ammonium ion, said compound being selected from the group consisting of the carbonates, the hydrogenocarbonates and the hydroxydes, and an aqueous solution containing, in the form of compounds selected from the group consisti,ng of the soluble salts and the soluble complexes (preferably soluble in an acid medium), copper, aluminum and zinc in such proportions that the atomic ratio $(Cu+Zn)/Al$ ranges from 0.20 to 2.10, preferably from 0.25 to 1.50, and the atomic ratio $Zn/Al$ ranges from 0.10 to 1.50, preferably from 0.15 to 1.20, said reaction taking place at a pH value usually ranging from 6.3 to 7.3, preferably from 6.7 to 7.1, at a temperature generally ranging from 45° to 65° C., preferably from 50° to 60° C., with an average time of residence in the reactor ranging from 0.1 to 60 minutes, preferably from 10 to 45 minutes , 2/ filtration, then water washing of the product obtained at the end of stage 1/, 3/ drying of the product obtained at the end of stage 2/, between 50° and 200° C., 4/ calcination of the product obtained at the end of stage 3/, between 250° and 500° C., preferably between 280° and 380° C.

Said mixing (or said compounding) is followed by:

filtering and water washing, then drying between 50° and 200° C., and afterwards calcining between 250° and 500° C., preferably between 280° and 380° C., if at least one of the two ternary cursors which have been mixed together has been previously obtained at the end of stage 1/ of one of the processes P and P' described above, drying between 50° and 200° C., then calcining between 250° and 500° C., preferably between 280° and 380° C., if one of the two ternary precursors which have been mixed together has been previously obtained at the end of stage 2/ of any one of processes P and P' described above, the other one of the two ternary precursors which have been mixed together being previously obtained at the end of one of stages 2/ to 4/ of one of the processes P and P, described above, or calcining between 250° and 500° C., preferably between 280° and 380° C., if the two ternary precursors which have been mixed together have been previously obtained at the end of one of stages 3/ and 4/ of one of the processes P and P' described above.

Thus, the process according to the invention can be implemented in accordance with numerous variants, which are referenced hereafter from A to J (for each variant, the stages forming said process are enumerated):

A:
- a/ co-precipitation reaction according to stage 1/ of process P previously described,
- b/ filtration, then water washing of the product obtained at the end of stage a/
- c/ co-precipitation reaction according to stage 1/ of process P' previously described,
- d/ filtration, then water washing of the product obtained at the end of stage c/,
- e/ mixing (or compounding) of the product obtained at the end of stage b/ with the product obtained at the end of stage d/,
- f/ drying of the product obtained at the end of stage e/, between 50° and 200° C.,
- g/ calcination of the product obtained at the end of stage f/ between 250° and 500° C., preferably between 280° and 380° C.

B:
- a/ co-precipitation reaction according to stage 1/ of process P previously described,
- b/ filtration, then water washing of the product obtained at the end of stage a/,
- c/ drying of the product obtained at the end of stage b/, between 50° and 200° C.,
- d/ co-precipitation reaction according to stage 1/ of process P' previously described,
- e/ filtration, then water washing of the product obtained at the end of stage d/,
- f/ drying of the product obtained at the end of stage e/, between 50° and 200° C.,
- g/ mixing (or compounding) of the product obtained at the end of stage c/ with the product obtained at the end of stage f/,
- h/ calcination of the product obtained at the end of stage g/ between 250° and 500° C., preferably between 280° and 380° C.

C:
- a/ co-precipitation reaction according to stage 1/ of process P previously described,
- b/ filtration, then water washing of the product obtained at the end of stage a/,
- c/ drying of the product obtained at the end of stage b/, between 50° and 200° C.,
- d/ calcination of the product obtained at the end of stage c/, between 250° and 500° C., preferably between 280° and
- e/ co-precipitation reaction according to stage 1/ of process P' previously described,
- f/ filtration, then water washing of the product obtained at the end of stage e/,
- g/ drying of the product obtained at the end of stage f/, between 50° and 200° C.,
- h/ calcination of the product obtained at the end of stage g/, between 250° and 500° C., preferably between 280° and 380° C.,
- i/ mixing (or compounding) of the product obtained at the end of stage d/ with the product obtained at the end of stage h/,
- j/ calcination of the product obtained at the end of stage i/, between 250° and 500° C., preferably between 280° and 380° C.

D:
- a/ co-precipitation reaction according to stage 1/ of process P previously described,
- b/ filtration, then water washing of the product obtained at the end of stage a/,
- c/ drying of the product obtained at the end of stage b/, between 50° and 200° C.,
- d/ co-precipitation reaction according to stage 1/ of process P' previously described.
- e/ filtration, then water washing of the product obtained at the end of stage d/,
- f/ mixing (or compounding) of the product obtained at the end of stage c/ with the product obtained at the end of stage e/,
- g/ drying of the product obtained at the end of stage f/, between 50° and 200° C.,
- h/ calcination of the product obtained at the end of stage g/, between 250° and 500° C., preferably between 280° and 380° C.

E:
- a/ co-precipitation reaction according to stage 1/ of process P previously described,
- b/ filtration, then water washing of the product obtained at the end of stage a/,
- c/ drying of the product obtained at the end of stage b/, between 50° and 200° C.,
- d/ calcination of the product obtained at the end of stage c/, between 250° and 500° C., preferably between 280° and 380° C.,
- e/ co-precipitation reaction according to stage 1/ of process P' previously described,
- f/ filtration, then water washing of the product obtained at the end of stage e/,
- g/ mixing (or compounding) of the product obtained at the end of stage d/ with the product obtained at the end of stage f/,
- h/ drying of the product obtained at the end of stage g/, between 50° and 200° C.,
- i/ calcination of the product obtained at the end of stage h/, between 250° and 500° C., preferably between 280° and 380° C.

F:
- a/ co-precipitation reaction according to stage 1/ of process P' previously described.
- b/ filtration, then water washing of the product obtained at the end of stage a/,
- c/ drying of the product obtained at the end of stage b/, between 50° and 200° C.,
- d/ co-precipitation reaction according to stage 1/ of process P previously described,
- e/ filtration, then water washing of the product obtained at the end of stage d/,
- f/ mixing (or compounding) of the product obtained at the end of stage c/ with the product obtained at the end of stage e/,
- g/ drying of the product obtained at the end of stage f/, between 50° and 200° C.,
- h/ calcination of the product obtained at the end of stage g/, between 250° and 500° C., preferably between 280° and 380° C.

G:
- a/ co-precipitation reaction according to stage 1/ of process P' previously described,
- b/ filtration, then water washing of the product obtained at the end of stage a/,
- c/ drying of the product obtained at the end of stage b/, between 50° and 200° C.,
- d/ calcination of the product obtained at the end of stage c/, between 250° and 500° C., preferably between 280° and 380° C., e/ co-precipitation reaction according to stage 1/ of process P previously described,
f/ filtration, then water washing of the product obtained at the end of stage e/,
g/ mixing (or compounding) of the product obtained at the end of stage d/ with the product obtained at the end of stage f/,
h/ drying of the product obtained at the end of stage g/, between 50° and 200° C.,
i/ calcination of the product obtained at the end of stage h/, between 250° and 500° C., preferably between 280° and 380° C.

H:
a/ co-precipitation reaction according to stage 1/ of process P previously described,
b/ filtration, then water washing of the product obtained at the end of stage a/,
c/ drying of the product obtained at the end of stage b/, between 50° and 200° C.,
d/ calcination of the product obtained a the end of stage c/, between 250° and 500° C., preferably between 280° and 380° C.,
e/ co-precipitation reaction according to stage 1/ of process P' previously described,
f/ filtration, then water washing of the product obtained at the end of stage e/,
g/ drying of the product obtained at the end of stage f/, between 50° and 200° C.,
h/ mixing (or compounding) of the product obtained at the end of stage d/ with the product obtained at the end of stage g/,
i/ calcination of the product obtained at the end of stage h/, between 250° and 500° C., preferably between 280° and 380° C.

I:
a/ co-precipitation reaction according to stage 1/ of process P' previously described,
b/ filtration, then water washing of the product obtained at the end of stage a/,
c/ drying of the product obtained at the end of stage b/, between 50° and 200° C.,
d/ calcination of the product obtained at the end of stage c/, between 250° and 500° C., preferably between 280° and 380° C.,
e/ co-precipitation reaction according to stage 1/ of process P previously described,
f/ filtration, then water washing of the product obtained at the end of stage e/,
g/ drying of the product obtained at the end of stage f/, between 50° and 200° C.,
h/ mixing (or compounding) of the product obtained at the end of stage d/ with the product obtained at the end of stage g/,
i/ calcination of the product obtained at the end of stage h/, between 250° and 500° C., preferably between 280° and 380° C.

J:
a/ co-precipitation reaction according to stage 1/ of process P previously described,
b/ co-precipitation reaction according to stage 1/ of process P' previously described,
c/ mixing (or compounding) of the product obtained at the end of stage a/ with the product obtained at the end of stage b/,
d/ filtration, then water washing of the product obtained at the end of stage c/,
e/ drying of the product obtained at the end of stage d/, between 50° and 200° C.,
f/ calcination of the product obtained at the end of stage e/, between 250° and 500° C., preferably between 280° and 380° C.

In the processes according to the invention, at least one, preferably each drying stage can possibly be immediately followed by the grinding of the product obtained at the end of said drying stage, in order to obtain a product in the form of a powder the grain size of which is preferably smaller than 2 $\mu$m ($2.10^{-6}$m) (the grinding process being then performed between said drying stage and the stage following said drying stage). Such a grinding can be achieved between the drying stage and a mixing stage.

It may be advantageous that, in the processes according to the invention comprising two (respectively three) calcination stages, that the first (respectively at least one of the first two) calcination stage be immediately followed by the grinding of the product obtained at the end of said first calcination stage (respectively of said at least one of the first two calcination stages), in order to obtain a product in the form of a powder the grain size of which is preferably smaller than 2 $\mu$m ($2.10^{-6}$m) (the grinding process being then performed between said calcination stage and the stage following said calcination stage). Nevertheless, such a grinding can be planned immediately before at least one calcination stage.

The grinding can for example be performed in a grinder of the ALPINE type. Among the variants A to J previously described, variants A, B, C and J are preferred.

In said variants A to J, the stage of the mixing of two products (or ternary precursors) consists for example in mixing these two products together by means of a turbine usually showing a high shear rate, such as a turbine of the STARO type (suspending the two products in distilled water, then strong stirring by means of said turbine); this mixing or compounding stage can also be carried out in any appropriate mixer, for example in a V-shaped mixer.

The mixing of the two ternary precursors can also consist in precipitating one of said ternary precursors in a reactor in the presence of the other ternary precursor introduced into said reactor while suspended in water.

As a matter of fact, the object of the present invention is also a process for preparing a precursor, preferably hydroxycarbonated, of a catalyst containing copper, aluminum and zinc, at least 50%, preferably at least 65% and more preferably at least 85% by weight of said precursor being made up of the mixing of a phase called roderite consisting of copper, aluminum and zinc and showing an atomic ratio (Cu+Zn)/Al ranging from 3.5 to 16, preferably from 4 to 13 and an atomic ratio Zn/Al ranging from 1.6 to 6, preferably from 2 to 5, and of a phase called prespinel consisting of copper, aluminum and zinc and showing an atomic ratio (Cu+Zn)/Al ranging from 0.20 to 2.10, preferably from 0.25 to 1.50 and an atomic ratio Zn/Al ranging from 0.10 to 1.50, preferably from 0.15 to 1.20; said process is characterized in that said precursor results from the mixing together of two ternary precursors, each one of them comprising copper, aluminum and zinc, one of said ternary precursors containing at least 50%, preferably at least 65% and more preferably at least 85% by weight of roderite phase and the other one of said ternary precursors containing at least 50%, preferably at least 65% and more preferably at least 85% by weight of prespinel phase, and in that it comprises the following stages:

a/ stage corresponding to stage 1/ of process P (respectively P') previously described, b/ filtration, then water washing of the product obtained at the end of stage a/, c/ co-precipitation stage corresponding to stage 1/ of process P' (respectively P) previously described, except the fact that, besides the two solutions used for the co-precipitation, water (for example bi-permuted) in which the product obtained at the end of stage b/ is suspended has also been introduced into the reactor, preferably simultaneously to the introducing of said two solutions, in order to obtain a mixing of two products, the first one being obtained at the end of stage b/ (it is the product suspended in water), the second one having precipitated during the co-precipitation reaction constituting this stage c/ on the first one, d/ filtration, then water washing of the mixture of products obtained at the end of stage c/, e/ drying of the product obtained at the end of stage d/, between 50° and 200° C., f/ calcination of the product obtained at the end of stage e/, between 250° and 500° C., preferably between 280° and 380° C.

In each co-precipitation reaction contained in the processes according to the invention, the aqueous solution containing copper, aluminum and zinc is for example an aqueous solution of soluble oxides, of hydroxydes, of carbonates and/or of hydroxycarbonates, preferably soluble in an acid medium, of copper, aluminum and zinc (for example $CuCO_3-Cu(OH)_2$, $ZnCO_3,Zn(OH)_2$, $Al(OH)_3$, the nitrates, oxalates, tartrates, citrates, acetates, acetylacetonates), possibly of amine complexes (soluble in an ammoniacal medium) of copper and zinc, the nitrates being the soluble salts which are most often used in said co-precipitation reaction.

Said aqueous solution generally contains about 0.7 to 2 gram-atoms of the total metals (Cu+Al+Zn) per liter. The other solution that is utilized in the co-precipitation reaction generally contains about 0.7 to 3.2 gram-atoms of alkali cations and/or ammonium ions per liter.

Any technique and device known by the man skilled in the art concerning the co-precipitation can be used; thus, the two (or three) solutions utilized in each co-precipitation reaction can be introduced into the reactor following any order; it is preferred to add the two (or three) solutions simultaneously, while controlling their flow rates through the pH value measured in the reaction zone, into a reactor advantageously comprising an efficient stirring system.

It is preferably operated continuously; the working volume of the reactor may range from some liters to about 100 liters and the product obtained at the end of the co-precipitation reaction is generally continuously recovered, then fed onto a filter, for example a press-filter or a rotary filter where it is then washed with water (for example bi-permuted) once or several times.

Each drying stage can be carried out by any process known by the man skilled in the art. It can for example be performed by spray-drying; the product which is then obtained generally contains about 60 to about 80% by weight of potential oxides. It can also be achieved by stove-drying, under air scavenging, in order to bring back, if necessary, the content by weight of potential oxides to a rate between about 60 and 80%. Drying is generally achieved during a time which is sufficient for the content by weight of water in the product after drying to be for example lower than 10%. During a drying stage following a filtration and washing stage, it is recommended to avoid that stagnating of the precipitate in the presence of steam partial pressures close to the steam saturation pressure at the considered drying temperature; such treatments can lead to a partial dehydration of the precipitate with the crystallizing of cupric oxide into big crystallites.

Each calcination (or thermal activation) stage can be carried out in the presence of an inert gas generally containing 0 to 50% by volume of oxygen.

The last calcination stage of the processes according to the invention is generally performed during a time that is sufficient, for example at least 30 minutes, for obtaining an activated product which does generally not contain more than 12% by weight of volatile matters (the rate of volatile matters is for example measured by activating in the presence of air a given weight of product placed in a capsule and calcinated at 500°-600° C. for 4 hours).

The drying and thermal activation operations can be optionally combined by using techniques of flash roasting or spray calcination, the product being then sprayed in a combustion gas stream.

The precursor, preferably hydroxycarbonated, can be optionally prepared by carrying out only one co-precipitation reaction, which is then called mixed co-precipitation, in which the two ternary precursors, preferably hydroxycarbonated, are simultaneously precipitated in the same medium (and not separately as in the previously described processes); this particular process comprises the following stages:

1/ mixed co-precipitation reaction within a reactor previously containing water (for example bi-permuted) between an aqueous solution of at least one compound of a constituent selected from the group consisting of the alkali metals (such as sodium, potassium) and the ammonium ion, said compound being selected from the group consisting of the carbonates, the hydrogenocarbonates and the hydroxydes, and an aqueous solution containing, in the form of compounds selected from the group consisting of the soluble salts and the soluble complexes (preferably soluble in an acid medium), copper, aluminum and zinc in such proportions that the atomic ratio (Cu+Zn)/Al ranges from 0.9 to 5.1, preferably from 1.1 to 4.6, and the atomic ratio Zn/Al ranges from 0.7 to 3.1, preferably from 0.9 to 2.6, said reaction taking place at a pH value usually ranging from 6.3 to 7.3, preferably from 6.7 to 7.1, at a temperature generally ranging from 45° to 90° C., with an average time of residence in the reactor ranging from 0.1 to 60 minutes, preferably from 10 to 45 minutes, 2/ filtration, then water washing of the product obtained at the end of stage 1/, 3/ drying of the product obtained at the end of stage between 50° and 200° C., 4/ calcination of the product obtained at the end of stage 3/, between 250° and 500° C., preferably between 280° and 80° C.

The relative proportions in roderite phase and in prespinel phase of said precursor prepared according to this last process can be changed, for example by adjusting the operating temperature of the co-precipitation unit operation (stage 1/) ranging from 45° to 90° C.

Thus, for a temperature ranging from 45° to 65° C., said precursor will be generally rich in prespinel phase (the prespinel phase then representing for example at least 60% by weight of the total (prespinel phase + roderite phase)); for a temperature ranging from 70° to 90° C., said precursor will be generally rich in roderite phase (the roderite phase then representing for example at least 60% by weight of the total (prespinel phase + roderite phase)).

From the precursor, preferably hydroxycarbonated, prepared according to one of the processes of the present invention, a catalyst can be manufactured, for example according to the following stages:

1/ optional grinding of said precursor prepared according to one of the previously described processes, generally up to a grain size smaller than 1 mm, preferably than 0.5 mm, 2/ shaping of the product obtained at the end of stage 1/, by any process known by the man skilled in the art (extrusion, bowl granulation, oil drop, etc), possibly including a mixture of said product at the rate of 0.5-5% of its weight with at least one compound selected from the group consisting of graphite, stearic acid, the stearates, and optionally a porosity adjuvant selected among cellulose and the powders of vegetal origin containing some of it, the ammonium carbonates, the combustible textile filters and naphthalene, and said product can then be optionally pelletized into solid cylinders with diameters of 2-6 mm or into toric cylinders with outside diameters of 3-6 mm and inside diameters of 1-4 mm and a height of 2-6 mm, 3/ calcination of the product obtained at the end of stage 2/, generally between 250° and 500° C., preferably between 280° and 380° C.

Any process for preparing a catalyst from a precursor, preferably hydroxycarbonated, comprising for example a grinding and a shaping stage, an optional final calcination stage generally between 250° and 500° C., preferably between 280° and 380° C., can nevertheless be utilized.

Said catalyst prepared in that way comprises copper, zinc and aluminum in the following proportions by weight, in relation to the total weight of the metals present in said catalyst:

15 to 80%, preferably 20 to 70% of copper,
4 to 50%, preferably 4 to 40% of aluminum, and
10 to 70%, preferably 20 to 60% of zinc.

Said catalyst can be used in = the processes utilizing a balanced reaction of the carbon oxides CO and $CO_2$ with hydrogen because of its outstanding activity, selectivity and stability, and especially in the processes for producing methanol (or ethanol) from carbon oxides CO and $CO_2$ and hydrogen, and in the processes for decomposing at least one $C_1$ to $C_5$ primary alcohol (in particular methanol and/or ethanol) into carbon oxides CO and $CO_2$ and hydrogen.

Previously to being used in said processes, said catalyst is preferably pre-reduced by a mixture of inert gas (for example nitrogen) and of at least one reducing compound selected from the group consisting of hydrogen, carbon oxide, the $C_1$ to $C_5$ alcohols and aldehydes, the molar ratio reducing compound/(reducing compound + inert gas) ranging from 0.001:1 to 1:1.

The reduction temperature generally ranges from about 100° to 300° C., preferably from about 140° to 260° C; the total pressure usually ranges from about 0.1 to 10 MPa and preferably from about 0.1 to 6 MPa; the hourly space velocity usually ranges from about $10^2$ to $4.10^4$ hour$^{-1}$ and preferably from $5.10^2$ to $10^4$ hour$^{-1}$ (Normal Temperature and Pressure (NTP)).

The reduction is first carried out, for example between about 140° and about 160° C., in the presence of the reducing mixture cited above and with a molar ratio reducing gas/(reducing gas + inert gas) ranging from about 0.001 to 0.1 and preferably from about 0.005 to 0.05, during a time sufficient for the reducing gas concentrations to be the same at the reactor inlet and outlet (which proves that the first reduction stage is over); it is then advantageous in a second stage to increase the temperature as well as optionally the reducing gas concentration, and to continue the reduction in more severe thermal conditions.

The reduction temperature then ranges from about 160° to about 260° C., and the molar ratio reducing gas/(reducing gas + inert gas) then ranges from 0.01 to 1, preferably from 0.05 to 1, the pressures and the hourly space velocity remaining within the limits cited above.

The methanol synthesis reaction is generally achieved in the following operating conditions the pressure usually ranges from about 2 to 15 MPa and preferably from about 4 to 15 MPa, the molar ratio $H_2/(2CO + 3CO_2)$ advantageously ranges from about 0.4 to 10, preferably from about 0.5 to 4 when the reaction is performed in the presence of a gaseous phase, and preferably from about 0.5 to 1.5 when the reaction is performed in the presence of a liquid phase and a gaseous phase. The temperature ranges from about 200° to 300° C., preferably from about 210° to 270° C.

The hourly space velocity (expressed in NTP volume of gaseous mixture per volume of catalyst and per hour) usually ranges from about 1,500 to 60,000 h$^{-1}$ and preferably from about 2,000 to 20,000 h$^{-1}$.

The decomposition reaction of at least one $C_1$ to $C_5$ primary alcohol (in particular methanol and/or ethanol) is performed in the following operating conditions the pressure usually ranges from about 1 to 6 MPa and preferably from about 2 to 5 MPa. The temperature ranges from about 200° to 320° C., preferably from about 220° to 300° C.

The hourly space velocity of the charge (expressed in liter of charge per liter of catalyst and per hour) usually ranges from about 0.1 to 5 h$^{-1}$ and preferably from about 0.5 to 3 h$^{-1}$.

The following examples illustrate the invention without limiting the scope thereof.

EXAMPLES

In examples 1 to 5 hereunder, the roderite and prespinel precursors are optionally prepared in two separate reactors (reactors 1 and 2). At the end of the co-precipitation stage, the precursors respectively called R1 and P1 (stage 1) are thus obtained, washed (stage 2) to obtain the precursors respectively called R2 and P2, and optionally mixed together (precursor RP2). After the drying stage (stage 3), the roderite and prespinel precursors respectively called R3 and P3, or the precursor resulting from the drying of product RP2 (precursor RP3), are optionally calcined (stage 4), separately in order to obtain the products called R4 and P4, or after mixing together R3 and P3 (product RP4). This calcination is optionally followed by a shaping stage (stage 5, products R5, P5, RP5).

(What is called a roderite precursor is the precursor containing the roderite phase and what is called prespi-

EXAMPLE 1

Catalyst A (according to the invention)

The preparation of the roderite precursor R2 is first achieved as follows:

253.61 g of trihydrated copper nitrate (1.05 g.at Cu) 44.61 g of nonahydrated aluminum nitrate (0.12 g.at Al), 140.48 g of hexahydrated zinc (0.47 g.at Zn) are dissolved in 1.5 liter of bi-permuted water, in order to obtain a solution (solution I) containing 1.09 g.at of metals per liter.

226.14 g of disodic carbonate are separately dissolved in 4 liters of water. A solution II containing 1.07 g.at of sodium per liter is obtained.

The reaction is carried out in a 3 liter reactor working continuously. The two solutions I and II are simultaneously injected into the reactor previously containing 2.8 liters of bi-permuted water at a temperature ranging between 75° and 85° C. The temperature is maintained between 75° and 85° C. for the total duration of the precipitation. The residence time is about 35 mn.

The flow rates are controlled by the pH which ranges between 6.7 and 7.1 for the total duration of the reaction. The reaction product (product R1) is continuously recovered in another reactor, filtered and washed three times by 12 liters of water. At the end of this stage 2, precursor 2 containing at least 85% by weight of roderite phase is obtained.

Prespinel precursor P2 is then prepared as follows:

98.73 g of trihydrated copper nitrate (0.41 g.at Cu), 306.5 g of nonahydrated aluminum nitrate (0.82 g.at Al), 229.57 g of hexahydrated zinc (0.77 g.at Zn) are dissolved in 2 liters of bi-permuted water, in order to obtain a solution (solution I) containing 1 g.at of metals per liter.

275.31 g of disodic carbonate are separately dissolved in 4 liters of water. A solution II containing 1.03 g.at of sodium per liter is obtained.

The reaction is carried out in a 3 liter reactor working continuously. The two solutions I and II are simultaneously injected into the reactor previously containing 2.8 liters of bi-permuted water at a temperature ranging between 50° and 60° C. The temperature is maintained between 50° and 60° C. for the total duration of precipitation. The residence time is about 35 mn.

The flow rates are controlled by the pH which ranges between 6.7 and 7.1 for the total duration of the reaction. The reaction product (product P1) is continuously recovered in another reactor, filtered and washed three times by 12 liters of water. At the end of this stage 2, precursor P2 containing at least 85% by weight of roderite phase is obtained.

The catalyst precursor is then obtained by mixing the two precursors R2 and P2 by means of a turbine of the STARO type for 15 minutes, then the mixed product is suspended again in about 600 cm³ of bi-permuted water and dried in an atomizer of the BUCHI type (outlet temperature 150° C., average residence time t=1.5 second) in order to obtain product RP3 containing 70% by weight of oxides. The catalyst is then obtained by calcination under air at 300° C. (product RP4). The residual volatile matter content is then 5%.

The obtained powder is finally mixed together with 2% by weight of graphite, pelletized in cylinders with a diameter of 2.4 mm and a height of 2 mm, then activated at 300° C. under air. About 265 g of catalyst A are obtained.

EXAMPLE 2

Catalyst B (according to the invention)

The preparation of the roderite precursor R2 is first carried out as follows:

173.56 g of trihydrated copper nitrate (0.72 g.at Cu), 127.96 g of nonahydrated aluminum nitrate (0.34 g.at Al), 213.65 g of hexahydrated zinc (0.72 g.at Zn) are dissolved in 1.5 liter of bi-permuted water, in order to obtain a solution (solution I) containing 1.18 g.at of metals per liter.

245.0 g of disodic carbonate are separately dissolved in 4 liters of water. A solution II containing 1.16 g.at of sodium per liter is obtained.

The reaction is achieved in a 3 liter reactor working continuously. The two solutions I and II are simultaneously injected into the reactor previously containing 2.8 liters of bi-permuted water at a temperature ranging between 75 and 85° C. The temperature is maintained between 75° and 85° C. for the total duration of the precipitation. The residence time is about 35 mn.

The flow rates are controlled by the pH, which ranges between 6.7 and 7.1 for the total duration of the reaction. The reaction product (product R1) is continuously recovered in another reactor, filtered and washed three times by 12 liters of water. At the end of this stage 2, precursor R2 containing at least 85% by weight of roderite phase is obtained.

The prespinel precursor P2 is then prepared as follows:

23.9 g of trihydrated copper nitrate (0.1 g.at Cu), 316 g of nonahydrated aluminum nitrate (0.84 g.at Al), 40.7 g of hexahydrated zinc (0.13 g.at Zn) are dissolved in 1 liter of bi-permuted water, in order to obtain a solution (solution I) containing 1.08 g.at of metals per liter.

148.65 g of disodic carbonate are separately dissolved in 2 liters of water. A solution II containing 2.8 g.at of sodium per liter is obtained.

The reaction is carried out in a 3 liter reactor working continuously. The two solutions I and II are simultaneously injected into the reactor previously containing 2.8 liters of bi-permuted water at a temperature ranging between 50° and 60° C. The temperature is maintained between 50° and 60° C. for the total duration of the precipitation. The residence time is about 40 mn.

The flow rates are controlled by the pH, which ranges between 6.7 and 7.1 for the total duration of the reaction. The reaction product (product P1) is recovered continuously in another reactor, filtered and washed three times by 12 liters of water. At the end of this stage 2, precursor P2 containing at least 85% by weight of prespinel phase is obtained.

The catalyst precursor is then obtained by mixing for 20 minutes the two precursors R2 and P2 by means of a turbine of the STARO type for 15 minutes, then the mixed product is suspended again in about 600 cm³ of bi-permuted water and dried in an atomizer of the BUCHI type (outlet temperature=150° C., average residence time t=1.5 second) in order to obtain product RP3 containing 70% by weight of oxides. The catalyst is then obtained by calcination under air at 300° C. (product RP4). The residual volatile matter content is then 4%.

The obtained powder is finally mixed together with 2% by weight of graphite, pelletized into cylinders with a diameter of 2.4 mm and a height of 2 mm, then activated at 300° C. under air. About 195 g of catalyst B are obtained.

EXAMPLE 3

Catalyst C (according to the invention)

The preparation of the roderite precursor R3 is first carried out as follows:
 173.56 g of trihydrated copper nitrate (0.72 g.at Cu), 127.96 g of nonahydrated aluminum nitrate (0.34 g.at Al), 213.65 g of hexahydrated zinc (0.72 g.at Zn) are dissolved in 1.5 liter of bi-permuted water, in order to obtain a solution (solution I) containing 1.18 g.at of metals per liter.
 245.01 g of disodic carbonate are separately dissolved in 4 liters of water. A solution II containing 1.16 g.at of sodium per liter is obtained.

The reaction is achieved in a 3 liter reactor working continuously. The two solutions I and II are simultaneously injected into the reactor previously containing 2.8 liters of bi-permuted water at a temperature ranging between 75 and 85° C. The temperature is maintained between 75° and 85° C. for the total duration of the precipitation. The residence time is about 35 mn.

The flow rates are controlled by the pH, which ranges between 6.7 and 7.1 for the total duration of the reaction. The reaction product (product R1) is recovered continuously in another reactor, filtered and washed three times by 12 liters of water. At the end of this stage 2, precursor R2 containing at least 85% by weight of roderite phase is obtained. The precursor is then suspended again in about 250 cm$^3$ of bi-permuted water, then dried in an atomizer of the BUCHI type (outlet temperature 145° C., average residence time t=1.8 second). The obtained product R3 contains about 72% of oxides.

The prespinel precursor P3 is then prepared as follows:
 23.9 g of trihydrated copper-nitrate (0.1 g.at Cu), 316 g of nonahydrated aluminum nitrate (0.84 g.at Al), 40.7 g of hexahydrated zinc (0.13 g.at Zn) are dissolved in 1 liter of bi-permuted water, in order to obtain a solution (solution I) containing 1.08 g.at of metals per liter.
 148.65 g of disodic carbonate are separately dissolved in 2 liters of water. A solution II containing 2.8 g.at of sodium per liter is obtained.

The reaction is performed in a 3 liter reactor working continuously. The two solutions I and II are simultaneously injected into the reactor previously containing 2.8 liters of bi-permuted water at a temperature ranging between 50° and 60° C. The temperature is maintained between 50° and 60° C. for the total duration of the precipitation. The residence time is about 40 mn.

The flow rates are controlled by the pH, which ranges 6.7 and 7.1 during the total reaction. The reaction product (product P1) is recovered continuously in another reactor, filtered and washed three times by 12 liters of water. At the end of this stage 2, precursor P2 containing at least 85% by weight of prespinel phase is obtained. The precursor is then suspended again in about 150 cm$^3$ of water, then dried in an atomizer of the BUCHI type (outlet temperature 145° C., average residence time t=1.6 second). The obtained product P3 contains about 68% of oxides.

The two precursors R3 and P3 are mixed together for 2 hours in a V-shaped powder mixer, then the obtained mixture is ground to a grain size smaller than 1 micron in a grinder of the Alpine type where the product is recycled three times. The obtained mixture is calcined at 300° C. under air (product RP4). The residual volatile matter content is then 4%.

The obtained powder RP4 is finally mixed together with 2% by weight of graphite, pelletized into cylinders with a diameter of 2.4 mm and a height of 2mm, then activated at 300° C. under air. About 195 g of catalyst C are obtained.

EXAMPLE 4

Catalyst D (according to the invention)

The preparation of product R4 from the roderite precursor is first achieved as follows:
 182 31 g of trihydrated copper nitrate (0.75 g.at Cu), 80.18 g of nonahydrated aluminum nitrate (0.21 g.at Al), 252.47 g of hexahydrated zinc (0.85 g.at Zn) are dissolved in 1.5 liter of bi-permuted water, in order to obtain a solution (solution I) containing 1.21 g.at of metals per liter.
 250.42 g of disodic carbonate are separately dissolved in 4 liters of water. A solution II containing 1.18 g.at of sodium per liter is obtained.

The reaction is carried out in a 3 liter reactor working continuously. The two solutions I and II are simultaneously injected into the reactor previously containing 2.8 liters of bi-permuted water at a temperature ranging between 75° and 85° C. The temperature is maintained between 75° and 85° C. for the total duration of the precipitation. The residence time is about 35 mn.

The flow rates are controlled by the pH, which ranges between 6.7 and 7.1 for the total duration of the reaction. The reaction product (product R1) is recovered continuously in another reactor, filtered and washed three times by 12 liters of water. At the end of this stage 2, precursor R2 containing at least 85% by weight of roderite phase is obtained. Product R2 is then suspended again and spray-dried at 135° C. for 2 seconds (product R3 with 73% of oxides), then calcined at 300° C. under air in order to obtain product R4.

Product P4 from the prespinel precursor is then prepared as follows:
 200.95 g of trihydrated copper nitrate (0.83 g.at Cu), 384.55 g of nonahydrated aluminum nitrate (1.03 g.at Al), 67.77 g of hexahydrated zinc (0.23 g.at Zn) are dissolved in 2 liters of bi-permuted water, in order to obtain a solution (solution I) containing 1.05 g.at of metals per liter.
 287.33 g of disodic carbonate are separately dissolved in 4 liters of water. A solution II containing 1.35 g.at of sodium per liter is obtained.

The reaction is carried out in a 3 liter reactor working continuously. The two solutions I and II are simultaneously injected into the reactor previously containing 2.8 liters of bi-permuted water at a temperature ranging between 50° and 60° C. The temperature is maintained between 50° and 60° C. for the total duration of the precipitation. The residence time is about 35 mn.

The flow rates are controlled by the pH, which ranges between 6.7 and 7.1 for the total duration of the reaction. The reaction product (product P1) is recovered continuously in another reactor, filtered and washed three times by 12 liters of water. At the end of this stage 2, precursor P2 containing at least 85% by weight of prespinel phase is obtained.

Product P2 is then suspended again in about 500 cm³ of bi-permuted water and spray-dried at 130° C. for 2 seconds (product P3 with 70% of oxides), then calcined 2 hours at 300° C. under air in order to obtain product P4.

Products P4 and R4 are then mixed together for 2 hours in a V-shaped powder mixer, then the obtained mixture is ground to a grain size smaller than 1 micron in a grinder of the Alpine type where the product is recycled 3 times.

The mixture which is obtained is calcined again at 300° C. in order to obtain the product RP4 containing 5% of volatile matters, which is formed by mixing with 2% by weight of graphite, and pelletizing into cylinders with a diameter of 2.4 mm and a height of 2 mm. This stage is followed by a new activation at 300° C. under air. About 277 g of catalyst D are thus obtained.

EXAMPLE 5

Catalyst E (according to the invention)

The preparation of the roderite precursor R2 is first carried out as follows:

182.31 g of trihydrated copper nitrate (0.75 g.at Cu), 80.18 g of nonahydrated aluminum nitrate (0.21 g.at Al), 252.47 g of hexahydrated zinc (0.85 g.at Zn) are dissolved in 1.5 liter of bi-permuted water, in order to obtain a solution (solution I) containing 1.21 g.at of metals per liter.

250.42 g of disodic carbonate are separately dissolved in 4 liters of water. A solution II containing 1.18 g.at of sodium per liter is obtained.

The reaction is performed in a 3 liter reactor working continuously. The two solutions I and II are simultaneously injected into the reactor previously containing 2.8 liters of bi-permuted water at a temperature ranging between 75° and 85° C. The temperature is maintained between 75° and 85° C. for the total duration of the precipitation. The residence time is about 35 mn.

The flow rates are controlled by the pH, which ranges between 6.7 and 7.1 for the total duration of the reaction. The reaction product (product R1) is recovered continuously in another reactor, filtered and washed three times by 12 liters of water. At the end of this stage 2, precursor R2 containing at least 85% by weight of roderite phase is obtained.

200.95 g of trihydrated copper nitrate (0.83 g.at Cu), 84.55 g of nonahydrated aluminum nitrate (1.03 g.at Al), 67.77 g of hexahydrated zinc (0.23 g.at Zn) are dissolved in 2 liters of bi-permuted water, in order to obtain a solution (solution I) containing 1.05 g.at of metals per liter.

287.33 g of disodic carbonate are separately dissolved in 4 liters of water. A solution II containing 1.35 g.at of sodium per liter is obtained.

The product R2 prepared above is then suspended again in 1.5 liter of bi-permuted water (solution III).

The reaction is carried out in a 3 liter reactor working continuously. The three solutions I, II and III are simultaneously injected into the reactor previously containing 2.8 liters of bi-permuted water at a temperature ranging between 50° and 60° C. The temperature is maintained between 50° and 60° C. for the total duration of the precipitation. The residence time is about 25 mn.

The flow rates are controlled by the pH, which ranges between 6.7 and 7.1 for the total duration of the reaction. The reaction product is recovered continuously in another reactor, filtered and washed three times by 12 liters of water. At the end of this stage 2, the precursor RP2 containing at least 85% by weight of (prespinel phase+roderite phase) is obtained.

Product RP2 is then suspended again in about 0.5 liter of water, and spray-dried at 130° C. for 2 seconds (product RP3 with 70% of oxides), then calcined 2 hours at 300° C. under air in order to obtain the product RP4 containing 5% of volatile matters, which is formed by mixing with 2% by weight of graphite, and pelletizing in cylinders with a diameter of 2.4 mm and a height of 2 mm. This stage is followed by a new activation at 300° C. under air. About 277 g of catalyst E are thus obtained.

EXAMPLE 6

Catalyst F (comparison)

The preparation of the roderite precursor is first carried out as follows:

173.56 g of trihydrated copper nitrate (0.72 g.at Cu), 127.96 g of nonahydrated aluminum nitrate (0.34 g.at Al), 213.65 g of hexahydrated zinc (0.72 g.at Zn) are dissolved in 1.5 liter of bi-permuted water, in order to obtain a solution (solution I) containing 1.18 g.at of metals per liter.

245.01 g of disodic carbonate are separately dissolved in 4 liters of water. A solution II containing 1.16 g.at of sodium per liter is obtained.

The reaction is achieved in a 3 liter reactor working continuously. The two solutions I and II are simultaneously injected into the reactor previously containing 2.8 liters of bi-permuted water at a temperature ranging between 75° and 85° C. The temperature is maintained between 75° and 85° C. for the total duration of the precipitation. The residence time is about 35 mn.

The flow rates are controlled by the pH, which ranges between 6.7 and 7.1 for the total duration of the reaction. The reaction product (product R1) is recovered continuously in another reactor, filtered and washed three times by 12 liters of water. At the end of this stage 2, precursor R2 containing at least 85% by weight of roderite phase is obtained.

The precursor is then suspended again in about 250 cm³ of bi-permuted water, then dried in an atomizer of the BUCHI type (outlet temperature=145° C., average residence time t=2 seconds). The obtained product R3 contains about 68% of oxides.

Precursor R3 is then calcined at 300° C. under air (product R4). The residual volatile matter content is then 3%.

The obtained powder R4 is mixed together with 2% by weight of graphite, pelletized in cylinders with a diameter of 2.4 mm and a height of 2 mm, and then activated at 300° C. under air. About 133 g of catalyst F are thus obtained.

EXAMPLE 7

Catalyst G (comparison)

200.95 g of trihydrated copper nitrate (0.83 g.at Cu), 384.55 g of nonahydrated aluminum nitrate (1.03 g.at Al), 67.77 g of hexahydrated zinc (0.23 g.at Zn) are dissolved in 2 liters of bi-permuted water, in order to obtain a solution (solution I) containing 1.05 g.at of metals per liter.

287.33 g of disodic carbonate are separately dissolved in 4 liters of water. A solution II containing 1.35 g.at of sodium per liter is obtained.

The reaction is achieved in a 3 liter reactor working continuously. The two solutions I and II are simultaneously injected into the reactor previously containing 2.8 liters of bi-permuted water at a temperature ranging between 50° and 60° C. The temperature is maintained between 50° and 60° C. for the total duration of the precipitation. The residence time is about 35 mn.

The flow rates are controlled by the pH, which ranges between 6.7 and 7.1 for the total duration of the reaction. The reaction product (product P1) is recovered continuously in another reactor, filtered and washed three times by 12 liters of water. At the end of this stage 2, precursor P2 containing at least 85% by weight of prespinel phase is obtained.

Product P2 is then suspended again in about 500 cm³ of bi-permuted water and spray-dried at 130° C. for 2 seconds (product P3 with 70% of oxides), then calcined at 300° C. under air in order to obtain product P4, which is ground to a scale of 1 micron in an ALPINE grinder.

The obtained powder P4 is mixed together with 2% by weight of graphite, pelletized in cylinders with a diameter of 2.4 mm and a height of 2 mm, and then activated at 300° C. under air. About 136 g of catalyst G are thus obtained.

EXAMPLE 8

Catalyst H (comparison)

A solution containing 238.1 g of copper nitrate (0.99 g.at Cu), 238.14 g of hexahydrated zinc nitrate (0.86 g.at Zn) and 231.02 g of nonahydrated aluminum nitrate (0.62 g.at Al) dissolved in 2 liters of bi-permuted water is reacted with a solution (1.3 liter) of disodic carbonate (339.6 g), at a temperature of 85° C.

The precipitate is then admixed with 50° g of sodium hydroxide in the form of pellets, and the mixture is made boil for 30 minutes.

The precipitate treated thereby is then filtered and washed four times in 4 liters of bi-permuted water in order to remove the excess soluble salts and more particularly the excess hydroxyde and sodium carbonate. The precursor obtained thereby is then stove-dried at 110° C., and afterwards calcined at 380° C. for 4 hours in order to obtain catalyst H, and finally pelletized in the form of pellets with a height of 2 mm and a diameter of 2.4 mm, and afterwards activated at 380° C. under air.

EXAMPLE 9

Catalyst I (comparison)

390 g of sodium aluminate are dissolved in 2 liters of bi-permuted water and 1.1 liter of a 70% by weight nitric acid solution is added. 597 g of hexahydrated zinc nitrate dissolved in 6 liters of water are then added to this solution.

The resulting solution is heated up to 85° C. and introduced into a stirred reactor, simultaneously to a molar solution of sodium carbonate previously heated up to 85° C. by means of pumps controlled by the pH. The pH value of the solution is maintained at pH 6.5 and the temperature is maintained at 65° C. A precipitate is thus obtained, which is filtered and washed.

Part of this precipitate (1,390 g) is suspended again in 3 liters of water and mixed with a solution containing 435 g of trihydrated copper nitrate and 134 g of zinc nitrate. A molar solution of sodium carbonate previously heated up to 85° C. is added to this mixture heated up to 85° C. in a stirred reactor.

The pH value of the solution is maintained at pH=6.5 and the temperature is maintained at 65° C. by controlling the flow rate of the pumps allowing to supply the nitrate and the carbonate solutions. The obtained mixture is ripened by heating up to 85° C. within about 10 minutes, then by maintaining the temperature at 85° C. for 20 more minutes under gentle stirring. The precipitate is filtered, washed in order to obtain a sodium content lower than 0.1% (expressed in $Na_2O$), then dried during one night at 110° C. The product obtained thereby is calcined for 6 hours at 300° C., then ground to a grain size smaller than 0.5 mm, and mixed with 2% by weight of graphite and pelletized in cylinders with a diameter of 2.4 mm and a height of 2 mm, and afterwards activated at 300° C. under air.

EXAMPLE 10

Catalyst J (comparison)

70.1 g of trihydrated copper nitrate (0.29 g.at Cu), 33.8 g of nonahydrated aluminum nitrate (0.09 g.at Al), 35.7 g of hexahydrated zinc (0.12 g.at Zn) are dissolved in 1 liter of bi-permuted water, in order to obtain a solution (solution I) containing 0.5 g.at of metals per liter.

70 g of disodic carbonate are separately dissolved in 0.7 liter of water. A solution II containing 1.9 g.at of sodium per liter is obtained.

The reaction is carried out in a 3 liter reactor containing 0.5 liter of bi-permuted water.

Solutions I and II are simultaneously fed into the reactor with a flow rate of 0.5 liter per hour. The temperature is maintained at 60° C. and the pH is maintained constant and equal to pH=7 by adjustment of the flow rate of the sodium carbonate solution. The precipitate is then ripened in the mother liquors at 25° C. for a night, and then filtered and washed with 2.5 liters of water. The washed precipitate is then dried at 75° C. and calcined 1 night under air at 350° C. The residual volatile matter content is then 2%.

The powder which is obtained through grinding below 0.5 mm is mixed together with 2% by weight of graphite, pelletized in cylinders with a diameter of 2.4 mm and a height of 2 mm, and then activated at 300° C. under air. 37 g of catalyst J are obtained.

EXAMPLE 11

Catalyst K (comparison)

30.3 g of trihydrated copper nitrate (0.13 g.at Cu), 45.2 g of nonahydrated aluminum nitrate (0.12 g.at Al), 76.2 hexahydrated zinc nitrate (0.26 g.at Zn) are dissolved in 1 liter of bi-permuted water, in order to obtain a solution (solution I) containing 0.5 g.at of metals per liter.

69 g of disodic carbonate are separately dissolved in 0.65 liter of water. A solution II containing 2 g.at of sodium per liter is obtained.

The reaction is carried out in a 3 liter reactor containing 0.5 liter of bi-permuted water.

Solutions I and II are simultaneously fed into the reactor with a flow rate of 0.5 liter per hour. The temperature is maintained at 80° C. and the pH is maintained constant and equal to pH=7 by adjusting the flow rate of the sodium carbonate solution. The precipitate is then ripened in the mother liquors at 80° C. for one night, and then filtered and washed with 2.5 liters of water at 80° C. The washed precipitate is then dried at 75° C. and calcined 1 night under air at 350° C. The residual volatile matter content is then 3%.

The powder obtained through grinding below 0.5 mm is mixed together with 2% by weight of graphite, pelletized in cylinders with a diameter of 2.4 mm and a height of 2 mm, and then activated at 300° C. under air. 37 g of catalyst K are obtained.

All the catalysts described in examples 1 to 11 are tested in the synthesis of methanol in the liquid phase, in a reactor with a diameter of 4 cm and a height of 3 meters.

The catalysts are previously reduced in situ in the gaseous phase by a mixture of hydrogen and nitrogen containing 6% of hydrogen in nitrogen, through successive temperature stages between 160 and 240° C. at the atmospheric pressure.

After the reduction, the solvent ($C_{12}$ to $C_{18}$ paraffinic cut) is introduced into the reactor at the rate of 270 liters per hour, simultaneously with the synthesis gas, under a pressure of 6 MPa. The gas and the liquid flow downwards and the operating conditions are the following:

Pressure: 6 MPa
Temperature: 215° C.
Ratio $H_2/(2CO+3CO_2)$: = 1
Hourly space volume: 15,800 $h^{-1}$ Table II shows the composition of the catalysts, the proportions relative to each element in the catalyst expressed in percentage by weight of metal in relation to the total weight of the metals, as well as the results of the tests in the liquid phase (for examples 1 to 11).

The performances are defined as follows:

Methanol mass productivity: it is the number of grams of methanol obtained per hour, in relation to the weight (in grams) of charged catalyst (prod)

Methanol selectivity: it is the ratio of the number of formed moles of methanol to the number of disappeared moles of (CO+$CO_2$).

The methanol selectivity SM is thus expressed as follows:

$$S_M = 100 \times \frac{\text{number of formed moles of methanol}}{\text{moles (CO + CO}_2\text{) inlet} - \text{moles (CO + CO}_2\text{) outlet}}$$

Number of rotation it is the number of moles of methanol obtained per hour, in relation to the accessible copper metallic surface $S_{Cu}$:

$$NR \text{ (moles} \cdot m^2 Cu^{-1} \cdot h^{-1}) = \frac{\text{number of formed moles of methanol per g of catalyst}}{S_{Cu}(m^2/g \cdot cat) \times \text{reaction time (h)}}$$

The metallic surface developed by copper in the catalysts of the present invention and the catalysts of the comparison examples has been determined from the dissociation of $N_2O$ at room temperature following the reaction:

$$2 Cu^\circ + N_2O \rightarrow Cu_2O + N_2$$

The catalyst is previously reduced in situ under hydrogen. The temperature increase velocity is 2° C./mn between the room temperature and 280° C. After a 1 hour-stage under hydrogen, the catalyst is desorbed under helium at 280° C. for 1 hour, then brought back to the room temperature. The chemisorption of $N_2O$ is then carried out according to the pulsed chromatography technique described by T. J. OSINGA et al (J. Catal. 7,277, 1967).

It can be seen from reading Table II that the catalysts prepared according to the invention (A to E) show better performances than the catalysts prepared according to prior art (F to K): as a matter of fact, thanks to catalysts A to E, it is possible to obtain a mass productivity and a number of rotation which are much higher, while having a methanol selectivity which is at least as good as with catalysts F to K.

EXAMPLE 12

Catalyst A is previously reduced in situ in the gaseous phase by a mixture of hydrogen and of nitrogen containing 6% of hydrogen in nitrogen, by successive temperature stages between 160 and 240° C. at atmospheric pressure.

After the reduction, the synthesis gas is injected into the reactor under a pressure of 6 MPa.

The operating conditions are the following:
Pressure: 6 MPa
Temperature: 215° C.
Ratio $H_2/(2CO+3CO_2)$: 1
Hourly space volume: 15,800 $h^{-1}$ The performances appear in Table II. It can be noticed that, even in the case of a process of synthesis of methanol in the gaseous phase, the catalyst A prepared according to the invention shows very good results.

EXAMPLE 13

In a tube-in-shell reactor, 10 g of catalyst A are reduced for several hours under atmospheric pressure by 5% of hydrogen in nitrogen between 140 and 260° C. After the reduction, the decomposition reaction of methanol is carried out. The mixture water-methanol admitted in the reactor contains 2 moles of water per mole of methanol.

For a temperature of 290° C., a pressure of 3 MPa and a liquid space velocity of $3h^{-1}$, more than 99% of the methanol are converted. The hydrogen yield, expressed by the ratio $$R = \frac{100 \times H}{3CH_3OH} \text{ (mol)}$$

exceeds 99%.

After 500 hours of operation, the performances are still the same.

Thus, the catalyst A prepared according to the invention shows very good results as for the decomposition of methanol for producing hydrogen.

TABLE II

| Example | Ref. | Catalysts Formula | Cu % | Al % | Zn % | $\frac{Cu + Zn}{Al}$ R | $\frac{Cu + Zn}{Al}$ P | $\frac{Zn}{Al}$ R | $\frac{Zn}{Al}$ P | $S_{Cu}$ | Prod. | $S_M$ (%) | NR |
|---|---|---|---|---|---|---|---|---|---|---|---|---|---|
| 1 | A | $Cu_{1.46}Al_{0.94}Zn_{1.24}$ | 46.6 | 12.7 | 40.7 | 12.7 | 1.5 | 4.0 | 0.9 | 33 | 1.45 | 99.5 | 1.40 |

TABLE II-continued

| Example | Catalysts Ref. | Formula | Cu % | Al % | Zn % | $\frac{Cu + Zn}{Al}$ | | $\frac{Zn}{Al}$ | | $S_{Cu}$ | Prod. | $S_M(\%)$ | NR |
|---|---|---|---|---|---|---|---|---|---|---|---|---|---|
| 2 | B | $Cu_{0.82}Al_{1.18}Zn_{0.85}$ | 37.3 | 22.8 | 39.8 | 4.2 | 0.3 | 2.1 | 0.2 | 27 | 1.18 | 99.6 | 1.37 |
| 3 | C | $Cu_{0.82}Al_{1.18}Zn_{0.85}$ | 37.3 | 22.8 | 39.8 | 4.2 | 0.3 | 2.1 | 0.2 | 23 | 1.02 | 99.5 | 1.38 |
| 4 | D | $Cu_{1.58}Al_{1.24}Zn_{1.08}$ | 49.1 | 16.4 | 34.5 | 7.5 | 1.0 | 4.0 | 0.2 | 32 | 1.34 | 99.4 | 1.31 |
| 5 | E | $Cu_{1.58}Al_{1.24}Zn_{1.08}$ | 49.1 | 16.4 | 34.5 | 7.5 | 1.0 | 4.0 | 0.2 | 35 | 1.55 | 99.7 | 1.38 |
| 6 | F | $Cu_{0.72}Al_{0.34}Zn_{0.72}$ | 44.8 | 9.0 | 46.2 | 4.2 | — | 2.1 | — | 20 | 0.64 | 99.3 | 1.00 |
| 7 | G | $Cu_{0.83}Al_{1.03}Zn_{0.23}$ | 55.2 | 29.1 | 15.7 | — | 1.0 | — | 0.2 | 27 | 0.82 | 98.5 | 0.95 |
|   |   |   |   |   |   | GLOBAL | | GLOBAL | |   |   |   |   |
| 8 | H | $Cu_{0.99}Al_{0.62}Zn_{0.86}$ | 46.3 | 12.3 | 41.4 | 3.0 | | 1.4 | | 20 | 0.55 | 99.2 | 0.86 |
| 9 | I | $Cu_{6.0}Al_{2.33}Zn_{1.67}$ | 68.9 | 11.4 | 19.7 | 3.3 | | 0.7 | | 27 | 0.95 | 98.8 | 1.10 |
| 10 | J | $Cu_{0.29}Al_{0.09}Zn_{0.12}$ | 64.2 | 8.5 | 27.3 | 4.6 | | 1.3 | | 24 | 0.84 | 99.2 | 1.09 |
| 11 | K | $Cu_{0.13}Al_{0.12}Zn_{0.26}$ | 28.9 | 11.4 | 59.6 | 3.2 | | 2.2 | | 15 | 0.50 | 99.4 | 1.04 |
|   |   |   |   |   |   | R | P | R | P |   |   |   |   |
| 12 | A | $Cu_{1.46}Al_{0.94}Zn_{1.24}$ | 46.6 | 12.7 | 40.7 | 12.7 | 1.5 | 4.0 | 0.9 | 33 | 1.31 | 99.6 | 1.24 |

(R = roderite phase. P = prespinel phase)

We claim:

1. In a catalytic process for reacting $CO_2$ and CO with hydrogen or for decomposing at least one $C_1$ to $C_5$ primary alcohol into CO and $CO_2$, the improvement comprising employing a catalyst comprising copper, zinc, and aluminum in the following proportions by weight in relation to the total weight of the metals present in said catalyst:

15 to 80% of copper,
4 to 50% of aluminum, and
10 to 70% of zinc, wherein said catalyst is prepared from a catalyst precursor containing copper, aluminum, and zinc, at least 50% by weight of said precursor being made up of the mixing of a roderite phase consisting of copper, aluminum, and zinc and showing an atomic ratio (Cu+Zn)/Al ranging from 3.5 to 16 and an atomic ratio Zn/Al ranging from 1.6 to 6, and of a prespinel phase consisting of copper, aluminum, and zinc and showing an atomic ratio (Cu+Zn)/Al ranging from 0.20 to 2.10 and an atomic ratio Zn/Al ranging from 0.1 to 1.50, characterized in that said precursor results from the mixing of two ternary precursors, each comprising copper, aluminum, and zinc, one of said ternary precursors containing at least 50% by weight of roderite phase and the other one of said ternary precursors containing at least 50% by weight of prespinel phase, said mixing taking place between, on one hand, one of the ternary precursors obtained at the end of one of stages (1) to (4) of a process P comprising the following stages:

(1) co-precipitation reaction between an aqueous solution of at least one compound of a constituent selected from the group consisting of the alkali metals and the ammonium ion, said compound being selected from the group consisting of the carbonates, the hydrogen carbonates, and the hydroxides, and an aqueous solution containing, in the form of compounds selected from the group consisting of the soluble salts and the soluble complexes, copper, aluminum, and zinc in such proportions that the atomic ratio (CU+Zn)/Al ranges from 3.5 to 16 and the atomic ratio Zn/Al ranges from 1.6 to 6, said reaction taking place at a pH value ranging from 6.3 to 7.3, at a temperature ranging from 70° to 90° C., with a residence time ranging from 0.1 to 60 minutes;

(2) filtration, then water washing of the product obtained at the end of stage (1);

(3) drying of the product obtained at the end of stage (2), between 50° to 200° C.;

(4) calcination of the product obtained at the end of stage (3), between 250° and 500° C.; and, on the other hand, one of the ternary precursors obtained at the end of one of stages (1) to (4) of a process P' comprising the following stages:

(1) co-precipitation reaction between an aqueous solution of at least one compound of a constituent selected from the group consisting of the alkali metals and the ammonium ion, said compound being selected from the group consisting of the carbonates, the hydrogen carbonates, and the hydroxides, and an aqueous solution containing, in the form of compounds selected from the group consisting of the soluble salts and the soluble complexes, copper, aluminum, and zinc in such proportions that the atomic ratio (Cu+Zn)/Al ranges from 0.20 to 2.10 and the atomic ratio Zn/Al ranges from 0.10 to 1.50, said reaction taking place at a pH value ranging from 6.3 to 7.3, at a temperature ranging from 45° to 65° C., with a residence timing ranging from 0.1 to 60 minutes;

(2) filtration, then water washing of the product obtained at the end of stage (1), (3) drying of the product obtained at the end of stage (2), between 50° and 200° C., said mixing being followed by:

filtering and water washing, then drying between 50° and 200° C. and, afterwards, calcining between 250° and 500° C., if at least one of the two ternary precursors which have been mixed together has been previously obtained at the end of stage (1) of one of the processes P and P';

drying between 50° and 200° C., then calcining between 250° and 500° C., if one of the ternary precursors which have been mixed together has been previously obtained at the end of stage (2) of any one of processes P and P', the other one of the two ternary precursors which have been mixed together being obtained at the end of one of stages (2) to (4) of one of the processes P and P'; and calcining between 250° and 500° C., if the two ternary precursors which have been mixed together have been previously obtained at the end of one of stages (3) and (4) of one of the processes P and P'.

2. A process according to claim 1, wherein the preparation of the catalyst comprises the further stages of:

1) grinding of resultant precursor in order to obtain a product in the form of a powder with a grain size smaller than 1 mm, 2) shaping of the product obtained at the end of stage 1), optionally including mixing said product at a rate of 0.5–5% by weight with at least one compound selected from the group consisting of graphite, stearic acid, the stearates, 3) calcination of the product obtained at the end of stage 2), between 250° and 500° C.

3. A process according to claim 1, wherein the preparation of the catalyst precursor comprises the following stages:
   a) co-precipitation reaction according to stage 1) of process P of claim 1,
   b) filtration, then water washing of the product obtained at the end of stage a),
   c) co-precipitation reaction according to stage 1) of process P' of claim 1,
   d) filtration, then water washing of the product obtained at the end of stage c),
   e) mixing of the product obtained at the end of stage g) with the product obtained at the end of stage d),
   f) drying of the product obtained at the end of stage e), between 50° and 200° C.,
   g) calcination of the product obtained at the end of stage f), between 250° and 500° C.

4. A process according to claim 1, characterized in that is comprises the following stages:
   a) co-precipitation reacting according to stage 1) of process P of claim 1, p1 b) filtration, then water washing of the product obtained at the end of stage a),
   c) drying of the product obtained at the end of stage b), between 50° and 200° C.,
   d) co-precipitation reaction according to stage 1) of process P of claim 1,
   e) filtration, then water washing of the product obtained at the end of stage d),
   f) drying of the product obtained at the end of stage e), between 50° and 200° C.,
   g) mixing of the product obtained at the end of stage c) with the product obtained at the end of stage f),
   h) calcination of the product obtained at the end of stage g), between 250° and 500° C.

5. A process according to claim 1, wherein the preparation of the catalyst precursor comprises the following stages:
   a) co-precipitation reaction according to stage 1) of process P of claim 1, p1 b) filtration, then water washing of the product obtained at the end of stage a),
   c) drying of the product obtained at the end of stage b), between 50° and 200° C.,
   d) calcination of the product obtained at the end of stage c), between 250° and 500° C.
   e) co-precipitation reaction according to stage 1) of process P' of claim 1,
   f) filtration, then water washing of the product obtained at the end of stage e),
   g) drying of the product obtained at the end of stage f), between 50° and 200° C.,
   h) calcination of the product obtained at the end of stage g), between 250° and 500° C.,
   i) mixing of the product obtained at the end of stage d) with the product obtained at the end of stage h),
   j) calcination of the product obtained at the end of stage i), between 250° and 500° C.

6. A process according to claim 1, wherein the preparation of the catalyst precursor comprises the following stages:
   a) co-precipitation reaction according to stage 1) of process P of claim 1, p1 b) filtration, then water washing of the product obtained at the end of stage a),
   c) drying of the product obtained at the end of stage b), between 50° and 200° C.,
   d) co-precipitation reaction according to stage 1) of process P' of claim 1,
   e) filtration, then water washing of the product obtained at the end of stage d),
   f) mixing of the product obtained at the end of stage c) with the product obtained at the end of stage e),
   g) drying of the product obtained at the end of stage f), between 50° and 200° C.,
   h) calcination of the product obtained at the end of stage g), between 250° and 500° C., 7. A process according to claim 1, wherein the preparation of the catalyst precursor comprises the following stages:
   a) co-precipitation reaction according to stage 1) of process P of claim 1, p1 b) filtration, then water washing of the product obtained at the end of stage a),
   c) drying of the product obtained at the end of stage b), between 50° and 200° C.,
   d) calcination of the product obtained at the end of stage c), between 250° and 500° C.,
   e) co-precipitation reaction according to stage 1) of process P' of claim 1,
   f) filtration, then water washing of the product obtained at the end of stage e),
   g) mixing of the product obtained at the end of stage d) with the product obtained at the end of stage f),
   h) drying of the product obtained at the end of stage g), between 50° and 200° C.,
   i) calcination of the product obtained at the end of stage h), between 250° and 500° C., 8. A process according to claim 1, wherein the preparation of the catalyst precursor comprises the following stags:
   a) co-precipitation reaction according to stage 1) of process P' of claim 1, p1 b) filtration, then water washing of the product obtained at the end of stage a),
   c) drying of the product obtained at the end of stage b), between 50° and 200° C.,
   d) co-precipitation reaction according to stage 1) of process P of claim 1, process P' of claim 1,
   e) filtration, then water washing of the product obtained at the end of stage d),
   f) mixing of the product obtained at the end of stage c with the product obtained at the end of stage e),
   g) drying of the product obtained at the end of stage f), between 50° and 200°,
   h) calcination of the product obtained at the end of stage g), between 250° and 500° C., 9. A process according to claim 1, wherein the preparation of the catalyst precursor comprises the following stages:
   a) co-precipitation reaction according to stage 1) of process P' of claim 1, p1 b) filtration, then water washing of the product obtained at the end of stage a),
   c) drying of the product obtained at the end of stage b), between 50° and 200° C.,
   d) calcination of the product obtained at the end of stage c), between 250° and 500° C.
   e) co-precipitation reaction according to stage 1) of process P' of claim 1, f) filtration, then water washing of the product obtained at the end of stage e), g) mixing of the product obtained at the end of stage d) with the product obtained at the end of stage f), h) drying of the product obtained at the end of stage g), between 50° and 200° C., i) calcination of the product obtained at the end of stage h), between 250° and 500° C., 10. A process according to claim 1, wherein the preparation of the catalyst precursor comprises the following stages:

a) co-precipitation reaction according to stage 1) of process P of claim 1, p1 b) filtration, then water washing of the product obtained at the end of stage a), c) drying of the product obtained at the end of stage b), between 50° and 200° C., d) calcination of the product obtained at the end of stage c), between 250° and 500° C.

e) co-precipitation reaction according to stage 1) of process P' of claim 1, f) filtration, then water washing of the product obtained at the end of stage e), g) drying of the product obtained at the end of stage f), between 50° and 200° C., h) mixing of the prodct obtained at the end of stage d) with the product obtained at the end of stage g), i) calcination of the product obtained at the end of stage h), between 250° and 500° C., 11. A process according to claim 1, wherein the preparation of the catalyst precursor comprises the following stages:

a) co-precipitation reaction according to stage 1) of process P' of claim 1, p1 b) filtration, then water washing of the product obtained at the end of stage a), c) drying of the product obtained at the end of stage b), between 50° and 200° C., d) calcination of the product obtained at the end of stage c), between 250° and 500° C.

e) co-precipitation reaction according to stage 1) of process P of claim 1, f) filtration, then water washing of the product obtained at the end of stage e), g) drying of the product obtained at the end of stage f), between 50° and 200° C., h) mixing of the product obtained at the end of stage d) with the product obtained at the end of stage g), i) calcination of the product obtained at the end of stage h), between 250° and 500° C., 12. A process according to claim 1, comprises the following stages:

a) co-precipitation reaction according to stage 1) of process P of claim 1, b) co-precipitation reaction according to stage 1) of process P' of claim 1, c) mixing of the product obtained at the end of stage a) with the product obtained at the end of stage b), d) filtration, then water washing of the product obtained at the end of stage c), e) drying of the product obtained at the end of stage d), between 50° and 200° C., f) calcination of the product obtained at the end of stage e), between 250° and 500° .

13. A process according to claim 1, comprising two calcination stages, wherein the first calcination stage is obtained at the end of said first calcination stage in order to obtain a product in the form of a powder with a grain size smaller than $2.10^{-6}$ m.

14. A process according to claim 1, comprising three calcination stages, wherein at least one of the first two calcination stages is immediately followed by the grinding of the product obtained at the end of said one of the first two calcination stages in order to obtain a product in the form of a powder with a grain size smaller than $2.10^{-6}$ m.

15. A process according to claim 1, wherein at least one drying stage is immediately followed by the grind of the product obtained at the end of said drying stage in order to obtain a product in the form of a powder with a grain size smaller than $2.10^{-6}$ m.

16. A process according to claim 1, wherein each drying stage is immediately followed by the grinding of the product obtained at the end of said drying stage in order to obtain a product in the form of a powder with a grain size smaller than $2.10^{-6}$ m.

17. The process according to claim 1, said precursor containing copper, aluminum and zinc, at least 65% by weight of said precursor consisting essentially of a mixture of roderite phase and of prespinel phase, said precursor resulting from the mixing of two ternary precursors each comprising copper, aluminum and zinc, one of said ternary precursors containing at least 65% by weight of roderite phase and the other one of said ternary precursors containing at least 65% by weight of prespinel phase.

18. A process according to claim 1, said precursor containing copper, aluminum and zinc, at least 85% by weight of said precursor consisting essentially of a mixture of roderite phase and of prespinel phase, said precursor resulting from the mixing of two ternary precursors each comprising copper, aluminum and zinc, one of said ternary precursors containing at least 85% by weight of roderite phase and the other one of said ternary precursors containing at least 85% by weight of prespinel phase.

19. A process according to claim 1 wherein said precursor is a hydroxycarbonated precursor and wherein said mixing is achieved between two hydroxycarbonated ternary precursors.

20. In a catalytic process comprising reacting CO and $CO_2$ with hydrogen, the improvement comprising employing a catalyst comprising copper, zinc, and aluminum in the following proportions by weight in relation to the total weight of the metals present in said catalyst:

15 to 80% of copper,
4 to 50% of aluminum, and
10 to 70% of zinc, wherein said catalyst is prepared from a catalyst precursor containing copper, aluminum, and zinc, at least 50% by weight of said precursor being made up of the mixing of a roderite phase consisting of copper, aluminum, and zinc and showing an atomic ratio $(Cu+Zn)/Al$ ranging from 3.5 to 16 and an atomic ratio $Zn/Al$ ranging from 1.6 to 6, and of a prespinal consisting of copper, aluminum, and zinc and showing an atomic ratio $(Cu+Zn)/Al$ ranging from 0.20 to 2.10 and an atomic ratio $Zn/Al$ ranging from 0.1 to 1.50, characterized in that said precursor results from the mixing of two ternary precursors, each comprising copper, aluminum, and zinc, one of said ternary precursors containing at least 50% by weight of roderite phase and the other one of said ternary precursors containing at least 50% by weight of prespinel phase, said mixing taking place between, on one hand, one of the ternary precursors obtained at the end of one of stages (1) to (4) of a process P comprising the following stages:

(1) co-precipitation reaction between an aqueous solution of at least one compound of a constituent selected from the group consisting of the alkali metal and the ammonium ion, said compound being selected from the group consisting of the carbonates, the hydrogen carbonates, and the hydroxides, and an aqueous solution containing, in the form of compounds selected from the group consisting of the soluble salts and the soluble complexes, copper, aluminum, and zinc in such proportions that the atomic ratio (Cu+Zn)/Al ranges from 3.5 to 16 and the atomic ratio Zn/Al ranges from 1.6 to 6, said reaction taking place at a pH value ranging from 6.3 to 7.3, at a temperature ranging from 70° C., with a residence time ranging from 0.1 to 60 minutes;

(b 2) filtration, then water washing of the product obtained at the end of stage (1);

(3) drying of the product obtained at the end of stage (2), between 50° and 200° C.;

(4) calcination of the product obtained at the end of stage (3), between 250° and 500° C.;

and, on the other hand, one of the ternary precursors obtained at the end of one of stages (1) to (4) of a process P' comprising the following stages:

(1) co-precipitation reaction between an aqueous solution of at least one compound of a constituent selected from the group consisting of the alkali metals and the ammonium ion, said compound being selected from the group consisting of the carbonates, the hydrogen carbonates, and the hydroxides, and an aqueous solution containing, in the form of compounds selected from the group consisting of the soluble salts and the soluble complexes, copper, aluminum, and zinc in such proportions that the atomic ratio (Cu+Zn)/Al ranges from 0.20 to 2.10 and the atomic ratio Zn/Al ranges from 0.10 to 1.50, said reaction taking place at a pH value ranging from 6.3 to 7.3, at a temperature ranging from 45° to 65° C., with a residence time ranging from 0.1 to 60 minutes;

(2) filtration, then water washing of the product obtained at the end of stage (1), (3) drying of the product obtained at the end of stage (2), between 50° and 200° C., (4) calcination of the product obtained at the end of stage (3), between 250° and 500° C., said mixing being followed by:

filtering and water washing, then drying between 50° and 200° C. and afterwards, calcining between 250° and 500° C., if at least one of the two ternary precursors which have been mixed together has been previously obtained at the end of stage (1) of one of the processes P and P';

drying between 50° and 200° C., then calcining between 250° and 500° C., if one of the ternary precursors which have been mixed together has been previously obtained at the end of stage (2) of any one of processes P and P', the other one of the two ternary precursors which have been mixed together being obtained at the end of one of stages (2) to (4) of one of the processes P and P'; and calcining between 250° and 500° C., if the two ternary precursors which have been mixed together have been previously obtained at the end of one of stages (3) and (4) of one of the processes P and P'.

21. A process according to claim 20 for producing methanol.

22. A process according to claim 21, wherein the preparation of the catalyst comprises the further stages of:

1) grinding of resultant precursor in order to obtain a product in the form of a powder with a grain size smaller than 1 mm, 2) shaping of the product obtained at the end of stage 1), optionally including mixing said product at a rate of 0.5–5% by weight with at least one compound selected from the group consisting of graphite, stearic acid, the stearates, 3) calcination of the product obtained at the end of stage 2), between 250° and 500° C.

23. A process according to claim 20, wherein the preparation of the catalyst comprises the further stages of:

1) grinding of resultant precursor in order to obtain a product in the form of a powder with a grain size smaller than 1 mm, 2) shaping of the product obtained at the end of stage 1), optional including mixing said product at a rate of 0.5–5% by weight with at least one compound selected from the group consisting of graphite, stearic acid, the stearates, 3) calcination of the product obtained at the end of stage 2), between 250° and 500° C.

* * * * *

UNITED STATES PATENT AND TRADEMARK OFFICE
CERTIFICATE OF CORRECTION

PATENT NO. : 5,112,591
DATED : May 12, 1992
INVENTOR(S) : Patrick CHAUMETTE et al.

It is certified that error appears in the above-identified patent and that said Letters Patent is hereby corrected as shown below:

On the Title page, item [75], After the third inventor's name; place of residence - - -

Reads. . . Maisons Lffitte
    SHOULD READ. . . Maisons Laffitte

IN THE CLAIMS: Claim 4; Line 4; delete after claim 1, "pl"
Claim 5; Line 5; after claim 1, delete "pl"
Claim 6; Line 5; after claim 1, delete "pl"
Claim 7; Line 5; after claim 1, delete "pl"
Claim 8; Line 5; after claim 1, delete "pl"
Claim 9; Line 5; after claim 1, delete "pl"
Claim 10; Line 5; after claim 1, delete "pl"
Claim 11; Line 5; after claim 1, delete "pl"

Signed and Sealed this

Twenty-ninth Day of June, 1993

Attest:

MICHAEL K. KIRK

*Attesting Officer*    *Acting Commissioner of Patents and Trademarks*